(12) United States Patent
Van Liesdonk et al.

(10) Patent No.: US 11,790,094 B2
(45) Date of Patent: *Oct. 17, 2023

(54) EVALUATION OF A MONITORING FUNCTION

(71) Applicant: KONINKLIJKE PHILIPS N.V., Eindhoven (NL)

(72) Inventors: Peter Petrus Van Liesdonk, Eindhoven (NL); Meilof Geert Veeningen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/578,549

(22) Filed: Jan. 19, 2022

(65) Prior Publication Data
US 2023/0008980 A1  Jan. 12, 2023

Related U.S. Application Data

(63) Continuation of application No. 16/633,418, filed as application No. PCT/EP2018/070530 on Jul. 30, 2018, now Pat. No. 11,232,218.
(Continued)

(51) Int. Cl.
*G06F 21/62* (2013.01)
*H04L 9/00* (2022.01)
(Continued)

(52) U.S. Cl.
CPC .......... *G06F 21/62* (2013.01); *G06F 21/6245* (2013.01); *H04L 9/008* (2013.01);
(Continued)

(58) Field of Classification Search
CPC ....... G06F 21/62; G06F 21/6245; H04L 9/08; H04L 63/0428; H04L 2209/46; H04W 12/02
See application file for complete search history.

(56) References Cited

U.S. PATENT DOCUMENTS 8,625,799 B2   1/2014  Loveland et al.
8,954,737 B2   2/2015  Brdiczka et al.
(Continued)

OTHER PUBLICATIONS

Myers, S. et al., "Threshold Fully Homomorphic Encryption and Secure Computation". IACR Cryptology ePrint Archive (2011), p. 454.

(Continued)

*Primary Examiner* — Chau Le

(57) ABSTRACT

According to one aspect, there is provided a server for use in evaluating a monitoring function to determine if a trigger condition is satisfied. The server comprises a processing unit and a memory unit. The memory unit is for storing a current monitoring state Ss of the server or an encrypted current monitoring state S of the monitoring function, the current monitoring state Ss of the server relating to the current monitoring state S of the monitoring function that is based on an evaluation of one or more previous events. The processing unit is configured to receive an indication of a first event from a first client node and evaluate the monitoring function to determine if the first event satisfies the trigger condition. The evaluation is performed using a privacy-preserving computation, PPC, with the server providing the current monitoring state Ss of the server as a first private input to the PPC or the encrypted current monitoring state S of the monitoring function as a first input to the PPC, and the first client node providing the first event or an encryption thereof as a private input to the PPC. The evaluation of the monitoring function provides an encrypted updated monitoring state S' of the monitoring function or an updated monitoring state Ss' of the server as an output of the monitoring function and an indication of whether the first event satisfies the trigger condition.

14 Claims, 5 Drawing Sheets

Related U.S. Application Data

(60) Provisional application No. 62/538,035, filed on Jul. 28, 2017.

(51) Int. Cl.
  *H04L 9/40* (2022.01)
  *H04W 12/02* (2009.01)

(52) U.S. Cl.
  CPC ...... *H04L 63/0428* (2013.01); *H04L 2209/46* (2013.01); *H04L 2209/50* (2013.01); *H04W 12/02* (2013.01)

(56) References Cited

U.S. PATENT DOCUMENTS

| | | | |
|---|---|---|---|
| 9,703,963 | B2 | 7/2017 | Roy |
| 10,191,754 | B2 | 1/2019 | Deng et al. |
| 10,268,834 | B2 | 4/2019 | Aljumah et al. |
| 2010/0017870 | A1* | 1/2010 | Kargupta ............ H04L 63/1408 709/201 |
| 2014/0310524 | A1* | 10/2014 | Yamanaka ............ H04L 63/123 713/170 |
| 2015/0039912 | A1 | 2/2015 | Edington et al. |
| 2019/0372768 | A1* | 12/2019 | Veeningen ................ H04L 9/14 |
| 2021/0157937 | A1 | 5/2021 | Van Liesdonk |

OTHER PUBLICATIONS

Bellare, M. et al., "Efficient Garbling from a Fixed-Key Blockcipher". IACR Cryptology ePrint Archive (2013), p. 426.
Chou, T. eet al., "The Simplest Protocol for Oblivious Transfer". Progress in Cryptology—LATINCRYPT 2015—4th International Conference on Cryptology and Information Security in Latin America, Guadalajara, Mexico, Aug. 23-26, 2016, Proceedings.
Cramer, R. et al., "Multiparty Computation from Threshold Homomorphic Encryption". In: Advances in Cryptology—EUROCRYP 2001, International Conference on the Theory and Application of Cryptographic Techniques, Innsbruck, Austria, May 6-10, 2001, Proceedings. Ed. by Birgit Pfitzmann, vol. 2045, Lecture Notes in Computer Science, Springer, 2001, pp. 280-299.
Diaz, D. et al., "A Systematic Framework for the Analysis and Development of Financial Market Monitoring Systems". 2011 Annual SRII Global Conference, Mar. 2011.
Gentry, C. "Fully homomorphic encryption using ideal lattices". In: Proceedings of the 41st Annual ACM Symposium an Theory of Computing, May 2009, pp. 169-178.
Laud, P. "Stateful Abstractions of Secure Multiparty Computation". In: ed. by Peeter Laud and Luna Kamm. vol. 13, Cryptology and Information Security Series IOS Press, 2015 Chap. 2, pp. 26-42.
Lindell, Y. et al., "A Proof of Security of Yao's Protocol for Two-Party Computation". In: J. Cryptology 22.2 (2009), pp. 161-188.
Lueks, W. et al., Revocable Privacy: Principles, Use Cases, and Technologies:. In Privacy Technologies and Policy—Thir Annual Privacy Forum, APF 2015, Luxembourg, Oct. 7-8, 2015, vol. 9484, Lecture Notes in Computer Sience, Springer, 2015, pp. 124-143.
Ramalingam, G. et al., "A Categorized Bibliography on Incremental Computation". In: Conference Record of the Twentieth Annual ACM Sigplan-Sigact Symposium on Principles of Programming Languages, Charleston, S.C., Jan. 1993. Ed. by Mary S. Van Deusen, ACM Press, 1993, pp. 502-510.
Wikipedia. Monitoring (medicine)—Wikipedia, The Free Encyclopedia. 2016.
International Search Report for PCT/EP2018/070530 dated Jul. 30, 2018.

* cited by examiner

EVALUATION OF A MONITORING FUNCTION

CROSS REFERENCE TO RELATED APPLICATION

The present application is a continuation of U.S. patent application Ser. No. 16/633,418, filed Jan. 23, 2020, which is the U.S. National Phase application under 35 U.S.C. § 371 of International Application No. PCT/EP2018/070530 filed Jul. 30, 2018, which claims the benefit of Provisional Application No. 62/538,035 filed Jul. 28, 2017. These applications are hereby incorporated by reference herein.

TECHNICAL FIELD OF THE INVENTION

The invention relates to the evaluation of a monitoring function to determine if a trigger condition is satisfied, and in particular to a server and a client node for use in evaluating a monitoring function, and methods of operating the same.

BACKGROUND TO THE INVENTION

The recent developments of Big Data has given rise to an almost unlimited amount of data that can be potentially used to make better decisions. Data analysis algorithms make it possible to perform complex analysis of this data and find trends and anomalies. Such an analysis allows refined conclusions about current events and predictions about future events to be made. This could lead to a huge impact in domains such as healthcare (for example based on an analysis of patient information) and finance (for example based on an analysis of trading data).

However, the data to be the subject of this sort of data analysis is often collected by a wide variety of companies and institutions, for a wide variety of reasons, and is not typically available in a single location where it can be analysed. There are many reasons why such information cannot easily be stored or combined in a single location. One obvious concern is privacy; there are strong legal constraints on how privacy-sensitive information can be used (particularly for healthcare-related information), but other concerns are that certain data is valuable or classified, or the owner simply does not want to release it. These concerns are in direct conflict with a desire to perform data analysis.

In some forms of data analysis, it is desired to perform a continuous monitoring of events (e.g. data measurements) to determine if a new event meets a trigger condition, and if so to trigger an alert or other process. An example of a simple trigger condition could be "the reported value (event) is outside the allowed bandwidth or range". An example of a more complex trigger condition could be "the reported value (event) is not within one standard deviation of the mean of the last 1000 entries", to "the extrapolated prognosis over data reported in the last half year forecasts disaster for next year".

Therefore there is a need for improved techniques for evaluating a monitoring function to determine if a trigger condition is satisfied when one or more of the parties involved is unwilling or unable to share relevant information, such as event information.

Reference is hereby made to US patent application 2014/310524 A1, "Data management device, power usage calculation system, data management method, and computer program product".

SUMMARY OF THE INVENTION

Privacy-preserving computation (PPC) allows the computation of a joint function on sensitive (private) inputs from mutually distrusting parties without requiring those parties to disclose these inputs to a trusted third party. In general terms, a typical problem in privacy/security is that party A has a value X1 and party B has a value X2, and both parties wish to keep their values secret from the other party, but they also want to compute a certain function $f:(Y1,Y2)=f(X1, X2)$, where output Y1 should go only to party A and output Y2 should only go to party B. PPC allows this problem to be addressed, and so PPC could—at least in theory—solve the problem of combining various datasets in a single analysis, without the need to share the actual content of these datasets.

However, currently this analysis is static in the sense that all the data or datasets that are needed as an input to the analysis are available before the computation starts, and the computation gives an output on those particular inputs. This means that whenever the input data changes, the whole secure computation needs to be run again, so the current approaches are not particularly suitable for scenarios in which a new data event occurs and it needs to be evaluated against preceding events (for which a computation has already been completed).

Thus, the invention provides that monitoring can be implemented using incremental functions, with the evaluation of the monitoring function being performed using a privacy preserving computation. This provides the advantage that the party evaluating the monitoring function does not need to have access to all (or even most) of the input information required to complete the evaluation, which addresses issues with respect to the sharing of privacy-sensitive, competition-sensitive, company-proprietary, or classified data.

It will be appreciated that in these data analysis scenarios the party providing the input event to be evaluated may change over time (for example different parties may be measuring events, and each need to submit the events for analysis). Existing techniques for two-party computations assume that the two roles are fixed during the entire computation. In certain embodiments of the invention, one role is fixed (a server, for example) and the other role (a client, for example) can move between several parties due to the use of incremental functions.

According to a first aspect, there is provided a server for use in evaluating a monitoring function to determine if a trigger condition is satisfied, the server comprising a memory unit for storing a current monitoring state Ss of the server or an encrypted current monitoring state S of the monitoring function, the current monitoring state Ss of the server relating to the current monitoring state S of the monitoring function that is based on an evaluation of one or more previous events; and a processing unit configured to receive an indication of a first event from a first client node; evaluate the monitoring function to determine if the first event satisfies the trigger condition, wherein the evaluation is performed using a privacy-preserving computation, PPC, wherein the server provides the current monitoring state Ss of the server as a first private input to the PPC or the encrypted current monitoring state S of the monitoring function as a first input to the PPC, and the first client node provides the first event or an encryption thereof as a private input to the PPC, wherein the evaluation of the monitoring function provides an encrypted updated monitoring state S' of the monitoring function or an updated monitoring state Ss' of the server as an output of the monitoring function and an indication of whether the first event satisfies the trigger condition.

In some embodiments, the PPC is a computation in which the server does not share the current monitoring state Ss of the server with the first client node and in which the first client node does not share the first event with the server. Put another way, the PPC is a computation in which the server keeps the current monitoring state Ss of the server secret from the first client node and in which the first client node keeps the first event secret from the server.

In some embodiments, the PPC is a multi-party computation, MPC, with the server and the first client node. In some embodiments, the MPC is threshold homomorphic encryption, THE. In other embodiments, the PPC is Fully Homomorphic Encryption, FHE.

In some embodiments, the processing unit is further configured to output the indication of whether the first event satisfies the trigger condition.

In some embodiments, the evaluation of the monitoring function further provides a public output o of the monitoring function if the first event satisfies the trigger condition.

In some embodiments, the PPC can be a multi-party computation, MPC, with the first client node, wherein the first client node provides a current monitoring state Sc of the first client node as a second private input to the PPC, wherein the current monitoring state Ss of the server and the current monitoring state Sc of the first client node together form the encrypted current monitoring state S of the monitoring function.

In these embodiments, the memory unit can be for storing an encrypted current monitoring state Sc of a client node, and wherein the processing unit can be further configured to send the encrypted current monitoring state Sc of a client node to the first client node after receiving the indication of a first event.

In these embodiments, the evaluation of the monitoring function can provide an updated monitoring state Sc' of the first client node and an updated monitoring state Ss' of the server, wherein the updated monitoring state Sc' of the first client node and the updated monitoring state Ss' of the server together form an encrypted updated monitoring state S' of the monitoring function, wherein the processing unit can be further configured to receive, from the first client node, an encrypted updated monitoring state Esk(Sc') of the first client node following the evaluation of the monitoring function to determine if the first event satisfies the trigger condition; and store the encrypted updated monitoring state Esk(Sc') of the first client node in the memory unit.

In these embodiments, the processing unit can be further configured to receive an indication of a second event from a second client node; send the encrypted updated monitoring state Esk(Sc') of the first client node to the second client node; evaluate the monitoring function to determine if the second event satisfies the trigger condition, wherein the evaluation is performed using the PPC with the second client node, wherein the server provides the updated monitoring state Ss' of the server as a private input to the PPC and the second client node provides the second event or an encryption thereof and the updated monitoring state Sc' of the first client node as private inputs to the PPC, wherein the evaluation of the monitoring function provides a further updated monitoring state Ss" of the server as a private output of the monitoring function and an indication of whether the second event satisfies the trigger condition, wherein the further updated monitoring state Ss" of the server forms an encrypted further updated monitoring state S" of the monitoring function together with a further updated monitoring state Sc" of the second client node.

In alternative embodiments, the PPC is Threshold Homomorphic Encryption, THE, and the memory unit is further for storing a public key of a THE scheme and a first key share for a private key of the THE scheme, wherein the first key share can be combined with a second key share for the private key stored by the first client node to determine the private key.

In these THE embodiments, the evaluation of the monitoring function can provide the encrypted updated monitoring state S' of the monitoring function and the processing unit can be further configured to store the encrypted updated monitoring state S' of the monitoring function in the memory unit.

In these THE embodiments, the processing unit can be further configured to receive an indication of a second event from a second client node; send the encrypted updated monitoring state S' of the monitoring function to the second client node; evaluate the monitoring function to determine if the second event satisfies the trigger condition, wherein the evaluation is performed using the PPC, wherein the server provides the encrypted updated monitoring state S' of the monitoring function as a first private input to the PPC and the second client node provides the second event or an encryption thereof and the encrypted updated monitoring state S' of the monitoring function as second private inputs to the PPC, wherein the evaluation of the monitoring function provides an encrypted further updated monitoring state S" of the monitoring function as an output of the monitoring function and an indication of whether the second event satisfies the trigger condition.

In further alternative embodiments, the PPC is Fully Homomorphic Encryption, FHE, and the memory unit is further for storing a public key of a fully homomorphic encryption scheme.

In these FHE embodiments, the indication of the first event from the first client node can be an encrypted first event that is encrypted using the public key.

In these FHE embodiments, the evaluation of the monitoring function can provide an encrypted indication of whether the first event satisfies the trigger condition; wherein the processing unit is further configured to send the encrypted indication of whether the first event satisfies the trigger condition to the first client node for decryption.

In these FHE embodiments, the processing unit can be further configured to receive an encrypted second event that is encrypted using a public key of the FHE scheme from a second client node; evaluate the monitoring function to determine if the second event satisfies the trigger condition, wherein the evaluation is performed using the PPC, wherein the evaluation of the monitoring function provides an encrypted further updated monitoring state S" of the monitoring function as an output of the monitoring function and an encrypted indication of whether the second event satisfies the trigger condition; and send the encrypted indication of whether the second event satisfies the trigger condition to the second client node for decryption.

According to a second aspect, there is provided a method of operating a server to evaluate a monitoring function to determine if a trigger condition is satisfied, the server storing a current monitoring state Ss of the server or an encrypted current monitoring state S of the monitoring function, the current monitoring state Ss of the server relating to the current monitoring state S of the monitoring function that is based on an evaluation of one or more previous events; wherein the method comprises receiving an indication of a first event from a first client node; evaluating the monitoring function to determine if the first event satisfies the trigger condition, wherein the evaluation is performed using a privacy-preserving computation, PPC; wherein the server provides the current monitoring state Ss of the server as a first private input to the PPC or the encrypted current monitoring state S of the monitoring function as a first input to the PPC, and the first client node provides the first event or an encryption thereof as a private input to the PPC, wherein the evaluation of the monitoring function provides an encrypted updated monitoring state S' of the monitoring function or an updated monitoring state Ss' of the server as an output of the monitoring function and an indication of whether the first event satisfies the trigger condition.

In some embodiments, the PPC is a computation in which the server does not share the current monitoring state Ss of the server with the first client node and in which the first client node does not share the first event with the server. Put another way, the PPC is a computation in which the server keeps the current monitoring state Ss of the server secret from the first client node and in which the first client node keeps the first event secret from the server.

In some embodiments, the PPC is a multi-party computation, MPC, with the server and the first client node. In some embodiments, the MPC is threshold homomorphic encryption, THE. In other embodiments, the PPC is Fully Homomorphic Encryption, FHE.

In some embodiments, the method further comprises the step of outputting the indication of whether the first event satisfies the trigger condition.

In some embodiments, the step of evaluating the monitoring function further provides a public output o of the monitoring function if the first event satisfies the trigger condition.

In some embodiments, the PPC can be a multi-party computation, MPC, with the first client node, wherein the first client node provides a current monitoring state Sc of the first client node as a second private input to the PPC, wherein the current monitoring state Ss of the server and the current monitoring state Sc of the first client node together form the encrypted current monitoring state S of the monitoring function.

In these embodiments, the method further comprises the step of storing an encrypted current monitoring state Sc of a client node in a memory unit of the server, and wherein the method further comprises the step of sending the encrypted current monitoring state Sc of a client node to the first client node after receiving the indication of a first event.

In these embodiments, the step of evaluating the monitoring function can provide an updated monitoring state Sc' of the first client node and an updated monitoring state Ss' of the server, wherein the updated monitoring state Sc' of the first client node and the updated monitoring state Ss' of the server together form an encrypted updated monitoring state S' of the monitoring function, wherein the method further comprises the steps of receiving, from the first client node, an encrypted updated monitoring state Esk(Sc') of the first client node following the evaluation of the monitoring function to determine if the first event satisfies the trigger condition; and storing the encrypted updated monitoring state Esk(Sc') of the first client node in the memory unit.

In these embodiments, the method further comprises the steps of receiving an indication of a second event from a second client node; sending the encrypted updated monitoring state Esk(Sc') of the first client node to the second client node; and evaluating the monitoring function to determine if the second event satisfies the trigger condition, wherein the evaluation is performed using the PPC with the second client node, wherein the server provides the updated monitoring state Ss' of the server as a private input to the PPC and the second client node provides the second event or an encryption thereof and the updated monitoring state Sc' of the first client node as private inputs to the PPC, wherein the step of evaluating the monitoring function provides a further updated monitoring state Ss" of the server as a private output of the monitoring function and an indication of whether the second event satisfies the trigger condition, wherein the further updated monitoring state Ss" of the server forms an encrypted further updated monitoring state S" of the monitoring function together with a further updated monitoring state Sc" of the second client node.

In alternative embodiments, the PPC is Threshold Homomorphic Encryption, THE, and the method further comprises the step of storing a public key of a THE scheme and a first key share for a private key of the THE scheme in a memory unit of the server, wherein the first key share can be combined with a second key share for the private key stored by the first client node to determine the private key.

In these THE embodiments, the step of evaluating the monitoring function can provide the encrypted updated monitoring state S' of the monitoring function and the method can further comprise the step of storing the encrypted updated monitoring state S' of the monitoring function in the memory unit.

In these THE embodiments, the method can further comprise the steps of receiving an indication of a second event from a second client node; sending the encrypted updated monitoring state S' of the monitoring function to the second client node; and evaluating the monitoring function to determine if the second event satisfies the trigger condition, wherein the evaluation is performed using the PPC, wherein the server provides the encrypted updated monitoring state S' of the monitoring function as a first private input to the PPC and the second client node provides the second event or an encryption thereof and the encrypted updated monitoring state S' of the monitoring function as second private inputs to the PPC, wherein the evaluation of the monitoring function provides an encrypted further updated monitoring state S" of the monitoring function as an output of the monitoring function and an indication of whether the second event satisfies the trigger condition.

In further alternative embodiments, the PPC is Fully Homomorphic Encryption, FHE, and the method further comprises the step of storing a public key of a fully homomorphic encryption scheme in a memory unit of the server.

In these FHE embodiments, the indication of the first event from the first client node can be an encrypted first event that is encrypted using the public key.

In these FHE embodiments, the step of evaluating the monitoring function can provide an encrypted indication of whether the first event satisfies the trigger condition; wherein the method further comprises the step of sending the encrypted indication of whether the first event satisfies the trigger condition to the first client node for decryption.

In these FHE embodiments, the method further comprises the steps of receiving an encrypted second event that is encrypted using a public key of the FHE scheme from a second client node; evaluating the monitoring function to determine if the second event satisfies the trigger condition, wherein the evaluation is performed using the PPC, wherein the evaluation of the monitoring function provides an encrypted further updated monitoring state S" of the monitoring function as an output of the monitoring function and an encrypted indication of whether the second event satisfies the trigger condition; and sending the encrypted indication of whether the second event satisfies the trigger condition to the second client node for decryption.

According to a third aspect, there is provided a computer program product comprising a computer readable medium having computer readable code embodied therein, the computer readable code being configured such that, on execution by a suitable computer or processor, the computer or processor is caused to perform any of the methods described above.

According to a fourth aspect, there is provided a first client node for use in evaluating a monitoring function to determine if a trigger condition is satisfied, the first client node comprising a processing unit configured to send an indication of a first event to a server, evaluate the monitoring function to determine if the first event satisfies the trigger condition, wherein the evaluation is performed using a privacy-preserving computation, PPC, with the server, wherein the server provides a current monitoring state Ss of the server or an encrypted current monitoring state S of the monitoring function as a first private input to the PPC and the first client node provides (i) a current monitoring state Sc of the first client node or an encryption of the current monitoring state S of the monitoring function; and (ii) the first event or an encryption thereof, as second private inputs to the PPC, wherein the evaluation of the monitoring function provides an encrypted updated monitoring state S' of the monitoring function or an updated monitoring state Sc' of the first client node as an output of the monitoring function and an indication of whether the first event satisfies the trigger condition.

In some embodiments, the PPC is a computation in which the server does not share the current monitoring state Ss of the server with the first client node and in which the first client node does not share the first event with the server. Put another way, the PPC is a computation in which the server keeps the current monitoring state Ss of the server secret from the first client node and in which the first client node keeps the first event secret from the server.

In some embodiments, the PPC is a multi-party computation, MPC, with the server and the first client node. In some embodiments, the MPC is threshold homomorphic encryption, THE.

In some embodiments, the processing unit is further configured to receive the indication of whether the first event satisfies the trigger condition from the server.

In some embodiments, the processing unit is further configured to receive a public output o of the monitoring function if the first event satisfies the trigger condition.

In some embodiments, the PPC is a multi-party computation, MPC, with the server, wherein the first client node provides a current monitoring state Sc of the first client node as a second private input to the PPC, wherein the current monitoring state Ss of the server and the current monitoring state Sc of the first client node together form the encrypted current monitoring state S of the monitoring function.

In some embodiments, the memory unit is configured to store a secret key, and wherein the processing unit is further configured to receive an encrypted current monitoring state Sc of a client node from the server after sending the indication of a first event; decrypt the encrypted current monitoring state Sc of a client node to determine the current monitoring state Sc; and use the current monitoring state Sc as the second private input to the PPC.

In these embodiments, the evaluation of the monitoring function can provide an updated monitoring state Sc' of the first client node and an updated monitoring state Ss' of the server, wherein the updated monitoring state Sc' of the first client node and the updated monitoring state Ss' of the server together form an encrypted updated monitoring state S' of the monitoring function, wherein the processing unit can be further configured to encrypt the updated monitoring state Sc' of the first client node; and send the encrypted updated monitoring state Esk(Sc') of the first client node to the server.

In some embodiments, the PPC is Threshold Homomorphic Encryption, THE, and the memory unit is further for storing a public key of a THE scheme and a second key share for a private key of the THE scheme, wherein the second key share can be combined with a first key share for the private key stored by the server to determine the private key.

In these THE embodiments, the evaluation of the monitoring function can provide the encrypted updated monitoring state S' of the monitoring function and, the processing unit can be further configured to discard the encrypted updated monitoring state S'.

In these THE embodiments, the processing unit can be further configured to receive an encrypted current monitoring state S of the monitoring function from the server after sending the indication of the first event; and use the encrypted current monitoring state S as the second private input to the PPC.

According to a fifth aspect, there is provided a method of operating a first client node to evaluate a monitoring function to determine if a trigger condition is satisfied, the method comprising sending an indication of a first event to a server, evaluating the monitoring function to determine if the first event satisfies the trigger condition, wherein the evaluation is performed using a privacy-preserving computation, PPC, with the server, wherein the server provides a current monitoring state Ss of the server or an encrypted current monitoring state S of the monitoring function as a first private input to the PPC and the first client node provides (i) a current monitoring state Sc of the first client node or an encryption of the current monitoring state S of the monitoring function; and (ii) the first event or an encryption thereof, as second private inputs to the PPC, wherein the evaluation of the monitoring function provides an encrypted updated monitoring state S' of the monitoring function or an updated monitoring state Sc' of the first client node as an output of the monitoring function and an indication of whether the first event satisfies the trigger condition.

In some embodiments, the PPC is a computation in which the server does not share the current monitoring state Ss of the server with the first client node and in which the first client node does not share the first event with the server. Put another way, the PPC is a computation in which the server keeps the current monitoring state Ss of the server secret from the first client node and in which the first client node keeps the first event secret from the server.

In some embodiments, the PPC is a multi-party computation, MPC, with the server and the first client node. In some embodiments, the MPC is threshold homomorphic encryption, THE.

In some embodiments, the method further comprises the step of receiving the indication of whether the first event satisfies the trigger condition from the server.

In some embodiments, the method further comprises the step of receiving a public output o of the monitoring function if the first event satisfies the trigger condition.

In some embodiments, the PPC is a multi-party computation, MPC, with the server, wherein the first client node provides a current monitoring state Sc of the first client node as a second private input to the PPC, wherein the current monitoring state Ss of the server and the current monitoring state Sc of the first client node together form the encrypted current monitoring state S of the monitoring function.

In some embodiments, the method further comprises the step of storing a secret key in a memory unit of the first client node, and wherein the method further comprises the steps of receiving an encrypted current monitoring state Sc of a client node from the server after sending the indication of a first event; decrypting the encrypted current monitoring state Sc of a client node to determine the current monitoring state Sc; and using the current monitoring state Sc as the second private input to the PPC.

In these embodiments, the step of evaluating the monitoring function can provide an updated monitoring state Sc' of the first client node and an updated monitoring state Ss' of the server, wherein the updated monitoring state Sc' of the first client node and the updated monitoring state Ss' of the server together form an encrypted updated monitoring state S' of the monitoring function, wherein the method further comprises the steps of encrypting the updated monitoring state Sc' of the first client node; and sending the encrypted updated monitoring state Esk(Sc') of the first client node to the server.

In some embodiments, the PPC is Threshold Homomorphic Encryption, THE, and the method further comprises the step of storing a public key of a THE scheme and a second key share for a private key of the THE scheme in a memory unit of the first client node, wherein the second key share can be combined with a first key share for the private key stored by the server to determine the private key.

In these THE embodiments, the step of evaluating the monitoring function can provide the encrypted updated monitoring state S' of the monitoring function and the method further comprises the step of discarding the encrypted updated monitoring state S'.

In these THE embodiments, the method further comprises the steps of receiving an encrypted current monitoring state S of the monitoring function from the server after sending the indication of the first event; and using the encrypted current monitoring state S as the second private input to the PPC.

According to a sixth aspect, there is provided a computer program product comprising a computer readable medium having computer readable code embodied therein, the computer readable code being configured such that, on execution by a suitable computer or processor, the computer or processor is caused to perform any of the methods described above.

According to a seventh aspect, there is provided a system for use in evaluating a monitoring function to determine if a trigger condition is satisfied, the system comprising a server as described above and at least one first client node as described above.

BRIEF DESCRIPTION OF THE DRAWINGS

Exemplary embodiments of the invention will now be described, by way of example only, with reference to the following drawings, in which.

DETAILED DESCRIPTION OF THE EMBODIMENTS

Figure 1:
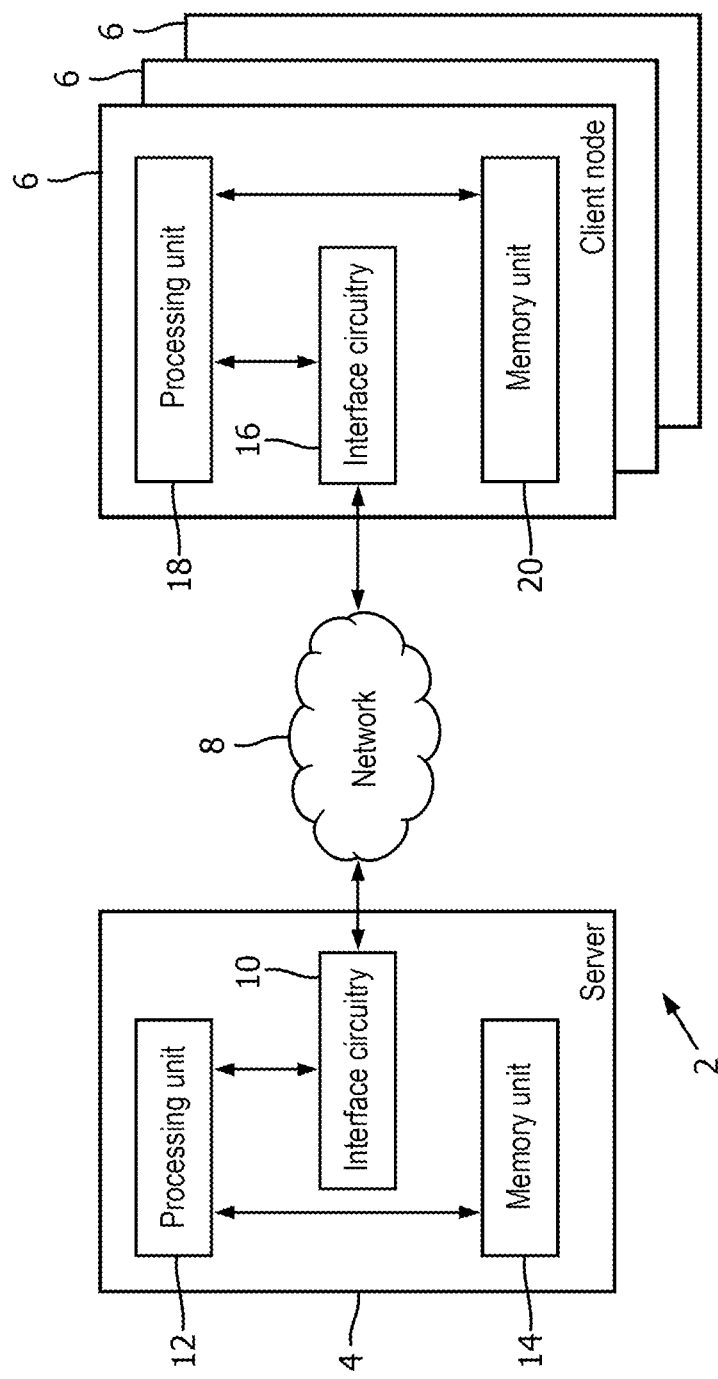
FIG. 1 is a block diagram of a system comprising a server and a plurality of client nodes.

FIG. 1 is a block diagram of a system 2 in which the techniques according to the invention can be implemented. The system 2 comprises a fixed party 4, which is referred to herein as a server 4, and one or more other parties 6, which are referred to herein as client nodes 6. Although FIG. 1 shows three client nodes 6, it will be appreciated that a system 2 can include more or less than three client nodes 6.

The server 4 is responsible for evaluating a monitoring function based on an event that is measured or observed by a client node 6. According to the invention this monitoring function is evaluated as a two-party privacy-preserving computation (PPC) with the server 4 being one of the parties and the client node 6 that has the event to be evaluated being the other party. If an event is subsequently measured or observed by a different one of the client nodes 6 (e.g. a second client node 6), the role of the server 4 in the computation does not change, and the other party is now the second client node 6. Thus, the server 4 is a fixed party 4 in the sense that the server 4 is always a party to the evaluation of the monitoring function, regardless of which client node 6 has an event to be evaluated.

The server 4 and client nodes 6 are interconnected via a network 8, such as the Internet, and thus may be located at respectively different locations. Of course, it will be appreciated that one or more of the client nodes 6 may be local to the server 8.

The server 4 (or more generally the fixed party 4) can be any type of electronic device or computing device that client nodes 6 can connect to in order to evaluate an event for those client nodes 6 with respect to a monitoring function.

A client node 6 can be any type of electronic device or computing device that can connect to a server 4 in order to evaluate an event for the client node 6 with respect to a monitoring function. For example a client node 6 can be a computer (including a server), laptop, tablet computer, smart phone, etc. It will be appreciated that the client node 6 does not have to measure or observe the event itself (e.g. it does not need to make the measurement of the patient parameter), but could receive the event from another device or retrieve the event from a database local to the client node 6.

The server 4 includes interface circuitry 10 for enabling a data connection to other devices, such as the client nodes 6. In particular the interface circuitry 10 can enable a connection between the server 4 and the network 8, such as the Internet, via any desirable wired or wireless communication protocol. The server 4 further includes a processing unit 12 for performing operations on data and for generally controlling the operation of the server 4. The server 4 further includes a memory unit 14 for storing any data required for the execution of the techniques described herein and for storing computer program code for causing the processing unit 12 to perform method steps as described in more detail below.

The processing unit 12 can be implemented in numerous ways, with software and/or hardware, to perform the various functions described herein. The processing unit 12 may comprise one or more microprocessors or digital signal processor (DSPs) that may be programmed using software or computer program code to perform the required functions and/or to control components of the processing unit 10 to effect the required functions. The processing unit 12 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

The memory unit 14 can comprise any type of memory, such as cache or system memory including volatile and non-volatile computer memory such as random access memory (RAM) static RAM (SRAM), dynamic RAM (DRAM), read-only memory (ROM), programmable ROM (PROM), erasable PROM (EPROM), and electrically erasable PROM (EEPROM).

Each client node 6 includes interface circuitry 16 for enabling a data connection to other devices, such as the server 4. In particular the interface circuitry 16 can enable a connection between the client node 6 and the network 8, such as the Internet, via any desirable wired or wireless communication protocol. The client node 6 further includes a processing unit 18 for performing operations on data and for generally controlling the operation of the client node 6. The client node 6 further includes a memory unit 20 for storing any data required for the execution of the techniques described herein and for storing computer program code for causing the processing unit 18 to perform method steps as described in more detail below.

The processing unit 18 and memory unit 20 can be implemented in numerous ways, similar to the processing unit 12 and memory unit 14 in the server 4.

In the techniques presented herein, the server 4 monitors successive events until a trigger condition has been met. The events are measured, observed or obtained by a variety of client nodes 6 that are mutually distrusting, and thus do not share events with each other. The events are assumed to be available for evaluation by the server 4 one at a time.

The following description of the invention refers to certain elements or terms, which are generally defined below.

Event—An event is a quantifiable observation or measurement reported by one of the client nodes 6. In some embodiments, the event is sent to the server 4 in encrypted form. As an example, an event could be the most recent values for systolic and diastolic blood pressure for a patient.

Trigger condition—The trigger condition is a predicate P that models the condition that the system 2/server 4 is monitoring for. The trigger condition, or rather whether the trigger condition is satisfied, may be dependent on all previous events (which may be of the same type) input by all client nodes 6 into the system 2/server 4. The predicate evaluates to true when the trigger condition is met or satisfied, and to false under all other conditions. An example of a trigger condition is "The average systolic blood pressure over the last 10 measurements is more than 120 mmHg OR the average diastolic blood pressure over the last 10 measurements is more than 80 mmHg."

Monitoring state—The monitoring state is a state S that contains information on previous events that have been evaluated. In some embodiments, it is stored by the server 4 in encrypted form. In other embodiments, information for reconstructing the state S can be stored in both the server 4 and a client node 6 (or nodes 6). The monitoring state S contains all the information necessary to evaluate the trigger condition given all event updates received so far.

Monitoring function—The monitoring function is a function f that evaluates the trigger condition predicate. Formally the monitoring function is a function that takes the current monitoring state S and the latest event $e_i$ as input and produces a new state S', a public bit t indicating whether the trigger condition is true (satisfied) and a public output o such that:

$$(t,o,S')=f(S,e_i) \tag{1}$$

where
$\{t=0, o=$empty if $P(e_1, \ldots, e_i)$ is false
$t=1, o=$public output if $P(e1, \ldots, ei)$ is true.

Such a function is called an incremental computation. In this invention the monitoring function is evaluated as or using a privacy preserving computation. The public output o is public in the sense that it is not encrypted and can indicate the result of the evaluation. For example the public output could be "the average systolic blood pressure has exceeded 120 mmHg", or a more detailed public output could be "the average systolic blood pressure over the last 10 measurements was 113 mmHg; the average diastolic blood pressure over the last 10 measurements was 93 mmHg".

Server—The server 4 is the entity that performs the actual monitoring, i.e. evaluation of the monitoring function. The server 4 receives new events from the client nodes 6, one at a time, in encrypted form, then evaluates the monitoring function with the help of the client node 6 that provided the event. The outputs t and o of this evaluation will be public information. In some embodiments, the server 4 stores (an encrypted version) of the updated monitoring state S', or stores a state associated with the server 4 that can be combined with a state associated with the client nodes 6 to reconstruct the updated monitoring state S'.

Client node—A client node 6 measures or obtains the information in an event and submits it to the server 4. There can be multiple client nodes 6 in the system 2, each of which independently submits events to the server 4. This can happen in any order; e.g. they can submit events according to a fixed schedule, or a client node 6 could submit many events before another client node 6 submits an event. It is assumed that the client nodes 6 communicate with the server 6 via a protected connection, i.e. they cannot learn each other's messages directly. An example of a client node 6 is the computer of a doctor or general practitioner (GP).

In this disclosure, 'monitoring' is considered as a repeated evaluation of the monitoring function f for every new event $e_i$, where the server 4 keeps or retains the monitoring state S between events. The monitoring function can be evaluated using privacy preserving computations (PPC), but such a computation requires at least two parties. Thus, every evaluation of the monitoring function is modelled as a two-party computation between the server 4 and the client node 6 that is submitting the latest event. In this two-party computation the client node 6 provides the event $e_i$ as a private input (i.e. an input that is kept secret or private from the other party in the computation), while the server 4 provides (an encryption of) the current state S as a private input. After computation, the server 4 will receive (an encryption of) the updated state S' as a private output (i.e. an output that is kept secret or private from the other party in the computation), and outputs t and o will be a public output (i.e. shared by the parties in the computation). For subsequent events, this process will repeat with the server 4 keeping the same role in the computation, but with a different client node 6 from event to event (namely the client node 6 that submitted the event).

Figure 2:
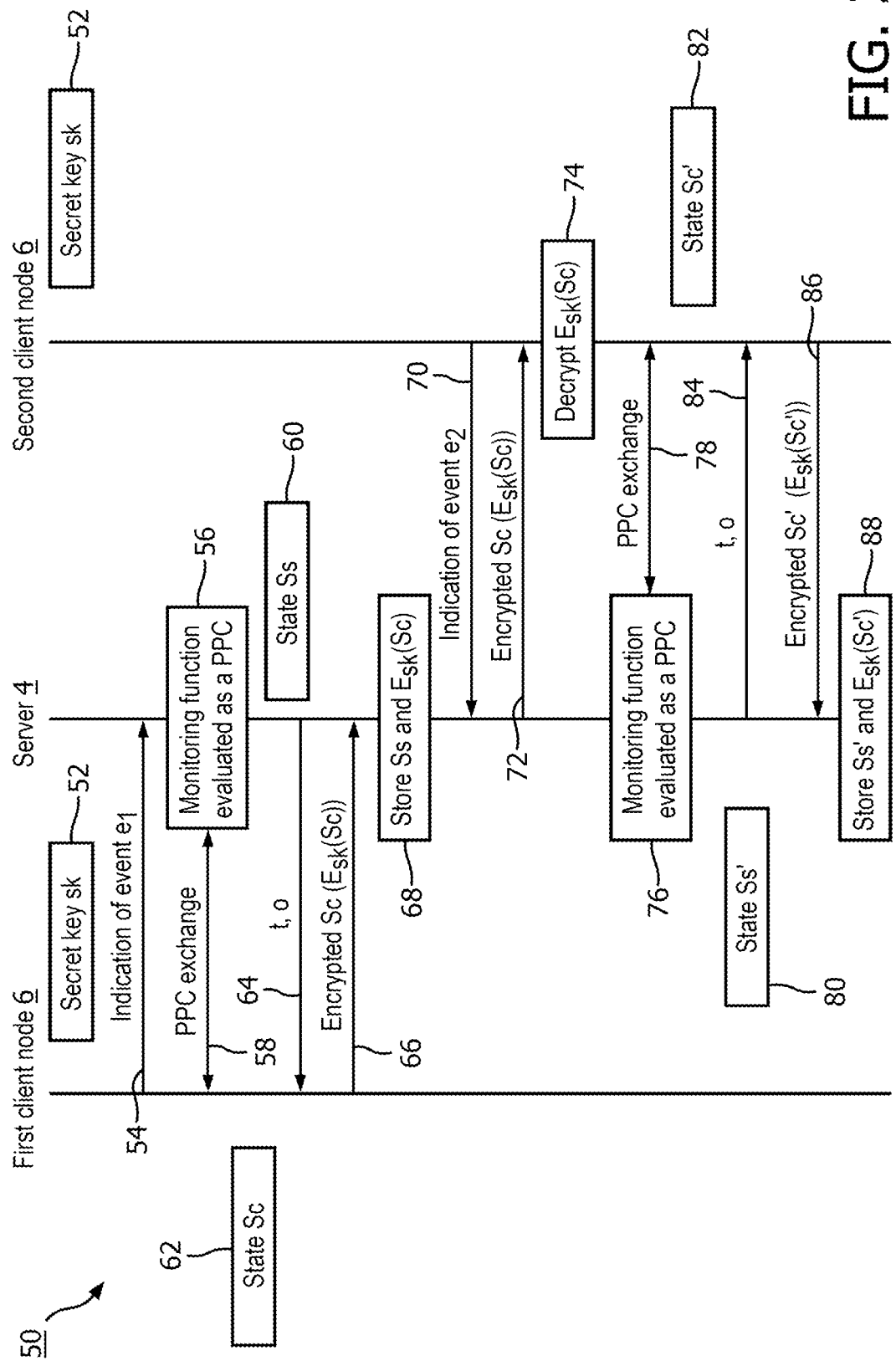
FIG. 2 is a signalling and flow diagram illustrating the operations of a server and two client nodes according to a generic embodiment of the invention.

Generic embodiment—A first exemplary embodiment of the techniques presented in this disclosure is described below with reference to FIG. 2. This first exemplary embodiment is referred to herein as the 'Generic' embodiment. FIG. 2 is a signalling and flow diagram that shows the information exchange and processing steps for a server 4 and a first client node 6 that submits a first event for evaluation. FIG. 2 also shows the information exchange and processing steps for the server 4 and a second client node 6 that submits a second event for evaluation.

In the Generic embodiment 50, the main idea is that all consecutive executions of the monitoring functions are performed as one big privacy preserving computation between the server 4 and a single hypothetical client node 6, with intermediate outputs after every event. This is considered as an 'incremental computation'. During this big computation both the server 4 and the client node 6 have a state, respectively Ss and Sc, that together form an encrypted version of the overall monitoring state S. This big computation is broken up after every output, and the control of the computation is passed to the next client node 6 by passing over the client node's state Sc to the next client node 6. This passing over of control happens indirectly, with help from the server 4.

Firstly, it is assumed that all client nodes 6 have a shared secret key sk (box 52 in FIG. 2). The server 4 does not have or have access to this secret key sk. Each client node 6 can store the secret key in the memory unit 20.

A client node 6 can start the generic two-party protocol with the server 4. At the start, it is assumed that neither the server 4 nor client node 6 have a current state in relation to the evaluation function to be monitored.

Firstly, a first client node 6 inputs an event $e_1$ that has been measured, observed or obtained by the first client node 6. The first client node 6 does not send the event $e_1$ to the server 4 directly, but instead indicates to the server 4 that an event is to be evaluated (signal 54).

Next, the server 4 evaluates the monitoring function as a privacy-preserving computation (PPC)—step 56. The PPC involves the exchange of information with the first client node 6 (signalling 58), without the first client node 6 sharing the first event $e_1$ with the server 4. Those skilled in the art will be aware of ways of evaluating functions as privacy-preserving computations, and thus further details are not provided herein. It will be appreciated that in some embodiments the indication of the event (signal 54) can be combined with the first message or signal of the PPC from the first client node 6 to the server 4, rather than being a separate message or signal.

The PPC of the monitoring function results in outputs t and o. As noted above, output t is an indication of whether the trigger condition is satisfied by the event $e_1$. If t=0 then output o will be empty. Outputs t and o are shared with the first client node 6 (signal 64). As a result of the PPC, the server 4 and first client node 6 end up with their own states Sc and Ss respectively (as indicated by boxes 60 and 62 respectively).

So that control of the computation can be passed by the server 4 to the next client node 6 to submit an event for evaluation, the first client node 6 encrypts their local state Sc using the secret key sk 52, resulting in $E_{sk}(Sc)$, and sends this to the server 4 (signal 66). The server 4 stores both Ss (the monitoring state of the server 4) and the encrypted state Sc of the first client node 6 ($E_{sk}(Sc)$) in a memory unit 14 (step 68). Since the server 4 does not know the secret key sk 52, the server 4 is not able to learn the contents of the client state Sc, which keeps the security of the protocol intact.

When another client node 6 (or even the first client node 6) has another event to evaluate, that client node 6 can continue the generic two-party protocol with the server 4 as follows. Thus, a second client node 6 has an event $e_2$ that has been measured, observed or obtained by the second client node 6. The second client node 6 indicates to the server 4 that an event is to be evaluated (signal 70).

The server 4 sends the encrypted client state $E_{sk}(Sc)$ stored in the memory unit 14 to the second client node 6 (signal 72). The second client node 6 decrypts the encrypted client state to find the current monitoring state Sc of the client nodes (with respect to the monitoring function f) using the secret key sk 52.

The server 4 and the second client node 6 then resume the privacy preserving computation to evaluate the second event $e_2$ according to the monitoring function (step 76, with information exchange shown by arrow 78), with the second client node 6 inputting the event $e_2$ and the current monitoring state Sc of the client node, and the server 4 inputting the current monitoring state Ss of the server 4.

The privacy preserving computation of the monitoring function results in outputs t and o, that are shared with the first client node 6 (signal 84). The server 4 and the second client node 6 end up with their own updated monitoring states Ss' and Sc' respectively (boxes 80 and 82 respectively.

Next, the second client node 6 encrypts the local monitoring state Sc' using sk 52, resulting in $E_{sk}(Sc')$, and the second client node 6 sends $E_{sk}(Sc')$ to the server 4 (signal 86). The server 4 stores both Ss' (the updated monitoring state of the server 4) and the encrypted state Sc' of the second client node 6 ($E_{sk}(Sc')$) in a memory unit 14 (step 88). Again, since the server 4 does not know the secret key sk 52, the server 4 is not able to learn the contents of the updated client node monitoring state Sc', which keeps the security of the protocol intact.

It will be appreciated that this generic embodiment is not able to guarantee security between client nodes 6 under all use cases, as the client node monitoring state Sc can contain unencrypted information from previous client nodes. However, for any natural privacy preserving computation of a monitoring function this will not be an issue.

The following embodiments address these concerns and provide security between client nodes 6.

Figure 3:
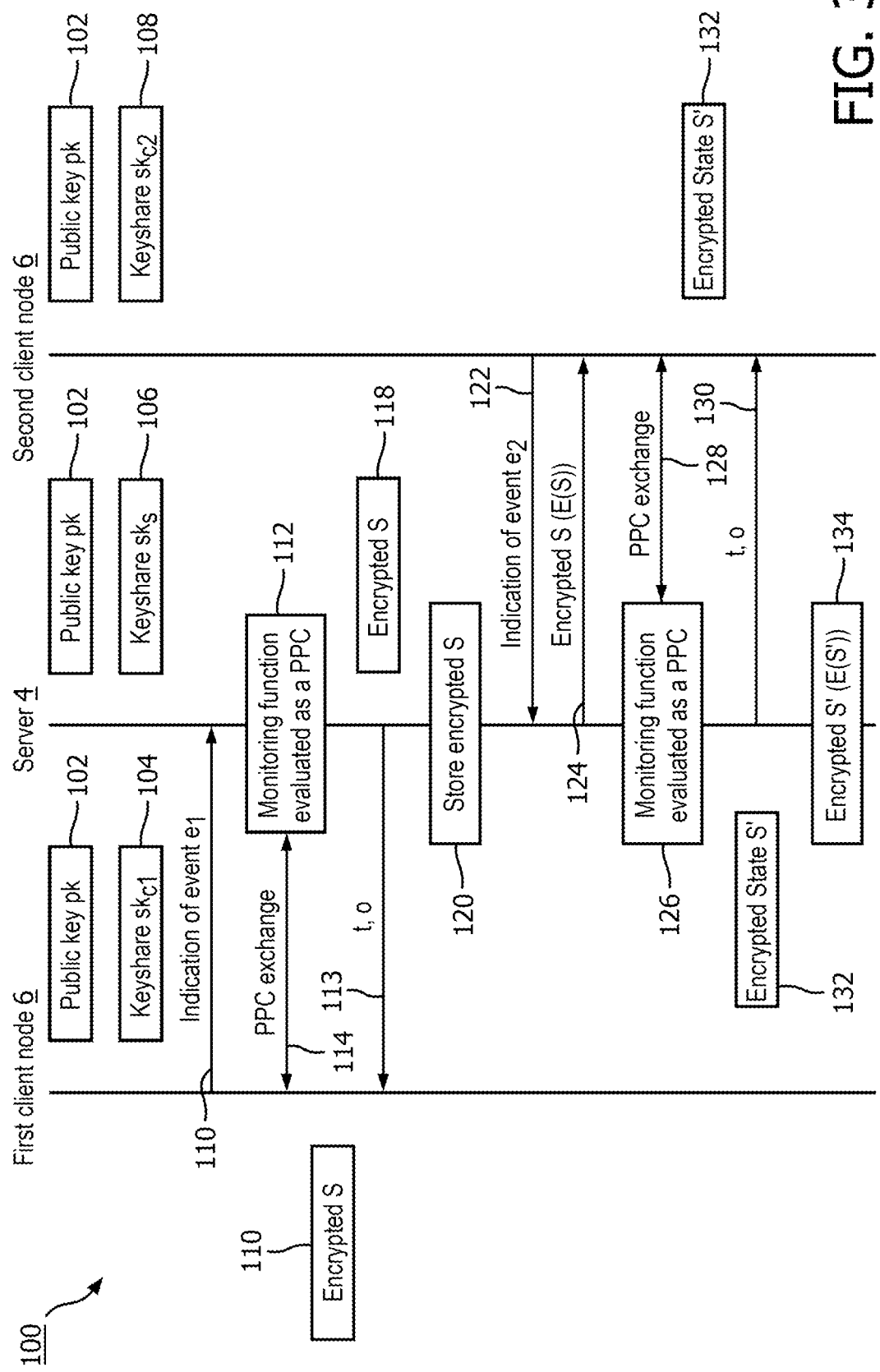
FIG. 3 is a signalling and flow diagram illustrating the operations of a server and two client nodes according to an embodiment of the invention in which the privacy-preserving computation is a Threshold Homomorphic Encryption (THE) scheme.

Threshold Homomorphic Encryption (THE)—A second exemplary embodiment of the techniques presented in this disclosure is described below with reference to FIG. 3. This second exemplary embodiment is referred to herein as the 'Threshold Homomorphic Encryption' embodiment 100 or the 'THE' embodiment 100. FIG. 3 is a signalling and flow diagram that shows the information exchange and processing steps for a server 4 and a first client node 6 that submits a first event for evaluation. FIG. 3 also shows the information exchange and processing steps for the server 4 and a second client node 6 that submits a second event for evaluation.

As is known, so-called 'threshold' encryption is similar to regular public/private key encryption in that there is one public key (so any party can make encryptions), but the (master) private key is split into multiple parts (where any number of parts can be used). This means that decryption is now only possible if a required amount of those key parts (also known as key shares) are used together. Splitting the private key can be as simple as part1=a random number and part2=secret−part1, which allows the private key to be reconstructed once both parts are known to a party.

Also as is known, homomorphic encryption is a specific type of encryption that allows some limited computations to be performed on encrypted data, while allowing the result to be found by decrypting the computation result. Usually this means that if there is an encryption of a number a, (E(a)) and an encryption of a number b (E(b)), the encryption E(a+b) can be found as E(a+b)=E(a)*E(b). However, it is not possible to compute E(a*b) without knowledge of the decryption key.

Threshold homomorphic encryption (THE) combines the properties of threshold encryption and homomorphic encryption, and allows interactions between the holders of the key-shares to perform the decryption, without actually bringing the key-shares together in a single party. THE also makes it possible to perform more complicated computations, since it is now possible to compute E(a+b) easily (via the homomorphic property) and E(a*b) with the use of those interactions. THE is one instance of Multi-Party Computation (MPC).

When the privacy preserving computation is performed using a threshold homomorphic encryption scheme, the generic embodiment shown in FIG. 2 can be simplified. In particular, the client node 6 and the server 4 do not each have their own independent monitoring state (i.e. Sc and Ss) that needs to be stored separately (or encrypted). Instead they each have a copy of the same state S, which is encrypted using threshold encryption. As a result, the monitoring state at the client node 6 after the PPC can be discarded. When a new event occurs (whether with the same client node 6 or another client node 6), that client node 6 can receive any required parts of the monitoring state from the server 4.

Firstly, the threshold homomorphic encryption scheme is set up, with the public key pk for the scheme available to the server 4 and all the client nodes 6. This is indicated by box 102 in FIG. 3.

The secret key sk required to decrypt data encrypted using the public key pk can be distributed between the server 4 and client nodes 6 in one of the following ways. In a first approach, the secret key sk is split once into two key shares. One key share (e.g. denoted $sk_s$) will be stored at the server 4 (e.g. in the memory unit 14) and the other key share (e.g. denoted $sk_c$) is used by all the client nodes 6. The client nodes 6 can store their key share in the memory unit 20). In a second approach, there can be different split of the secret key sk into two key shares for every client node 6. This means every client node 6 will have a different key share $sk_c$ to the other client nodes 6, and the server will have a corresponding key share $sk_s$, for every client node 6 (that can be used with the key share $sk_c$ for that client node 6 to recover the secret key sk and/or perform decryptions of data encrypted with the public key pk). Those skilled in the art of encryption will be aware of various ways in which these key shares and their distribution can be set up, so further details are not provided herein, although one approach could involve their creation and/or distribution using a trusted third party.

Thus, in FIG. 3 each of the server 4 and client nodes 6 has a key share for the secret key sk required to decrypt data encrypted using the public key pk. The first client node 6 has a key share $sk_{c1}$ (indicated by box 104), the server 4 has a key share $sk_s$ (box 106) for use with the key share $sk_{c1}$ of the first client node 6, and the second client node 6 has a key share denoted $sk_{c2}$ (box 108). Following the approaches described above, the key share $sk_{c2}$ of the second client node 6 will either be the same as that used by the first client node 6 (i.e. $sk_{c1}=sk_{c2}$), in which case the server 4 has a single key share $sk_s$, or the each client node 6 has their own key share (i.e. $sk_{c1} \neq sk_{c2}$), and the server 4 stores respective key shares for each client node 6.

Once the key shares have been distributed, a client node 6 can start the threshold homomorphic encryption protocol with the server 4. At the start, it is assumed that neither the server 4 nor client node 6 have a current state in relation to the evaluation function to be monitored.

Firstly, a first client node 6 inputs an event $e_1$ that has been measured, observed or obtained by the first client node 6. The first client node 6 does not send the event $e_1$ to the server 4 directly, but instead indicates to the server 4 that an event is to be evaluated (signal 110).

Next, the server 4 evaluates the monitoring function as a privacy-preserving computation (PPC)—step 112. The PPC involves the exchange of information with the first client node 6 (signalling 114), without the first client node 6 sharing the first event $e_1$ with the server 4. As noted above, those skilled in the art will be aware of ways of evaluating functions as privacy-preserving computations, and thus further details are not provided herein. It will be appreciated that in some embodiments the indication of the event (signal 110) can be combined with the first message or signal of the PPC from the first client node 6 to the server 4, rather than being a separate message or signal.

The PPC of the monitoring function results in outputs t and o. These outputs are public outputs (i.e. they are not encrypted), although it will be appreciated that the PPC will initially determine encrypted versions of t and o, and they will be decrypted as part of the PPC. As noted above, output t is an indication of whether the trigger condition is satisfied by the event $e_1$. If t=0 then output o will be empty. Outputs t and o are shared with the first client node 6 (signal 116). As a result of the PPC, the server 4 and first client node 6 both end up with the same (encrypted) monitoring state S (E(S), as indicated by boxes 118).

Next, the first client node 6 discards the encrypted state S (E(S)). The server 4 stores the encrypted state S (i.e. stores E(S))—step 120, so that it can send the current monitoring state of the monitoring function to the next client node 6 to submit an event for evaluation. The server 4 is not able to learn the contents of the monitoring state S, since it requires the first client node's key share ($sk_{c1}$) to decrypt encryptions of S.

When another client node 6 (or even the first client node 6) has another event to evaluate, that client node 6 can continue the THE protocol with the server 4 as follows. Thus, a second client node 6 has an event $e_2$ that has been measured, observed or obtained by the second client node 6. The second client node 6 indicates to the server 4 that an event is to be evaluated (signal 122).

The server 4 sends the encrypted monitoring state E(S) stored in the memory unit 14 to the second client node 6 (signal 124).

The server 4 and the second client node 6 then resume the privacy preserving computation to evaluate the second event $e_2$ according to the monitoring function (step 126, with information exchange shown by arrow 128), with the second client node 6 inputting the event $e_2$ and the encrypted current monitoring state E(S), and the server 4 inputting the encrypted current monitoring state E(S).

The privacy preserving computation of the monitoring function results in outputs t and o that are shared with the second client node 6 (signal 130). As above, these outputs are public outputs, i.e. they are not encrypted. The server 4 and the second client node 6 also both end up with the same (encrypted) updated monitoring state S' (denoted E(S')) as shown in box 132.

Next, the second client node 6 discards the encrypted updated state S' (E(S')). The server 4 stores the encrypted updated state S' (i.e. stores E(S'))—step 134, so that it can send the current monitoring state of the monitoring function to the next client node 6 to submit an event for evaluation. Again, the server 4 is not able to learn the contents of the updated monitoring state S', since it requires the second client node's key share ($sk_{c2}$) to decrypt encryptions of S'.

Figure 4:
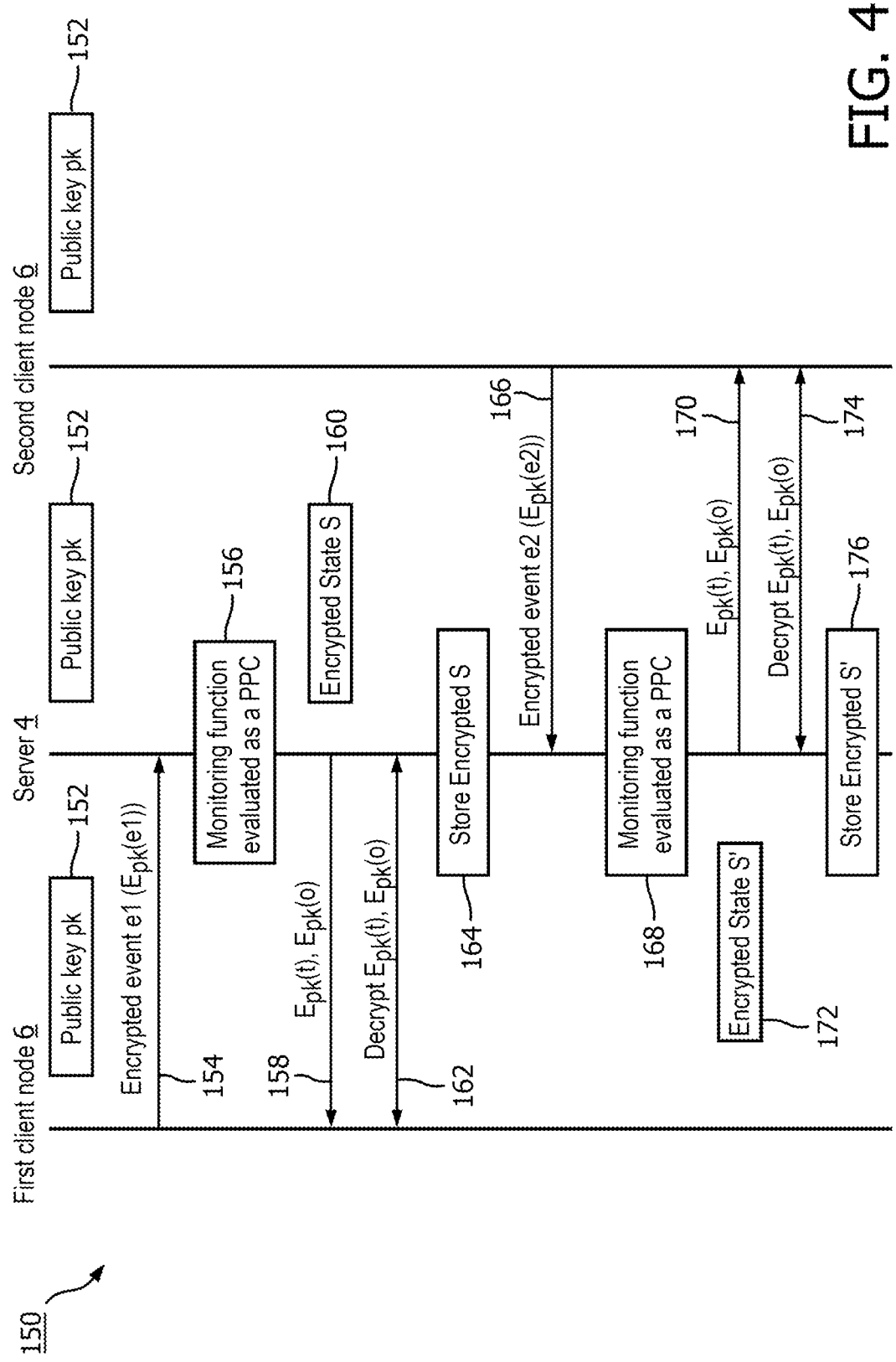
FIG. 4 is a signalling and flow diagram illustrating the operations of a server and two client nodes according to an embodiment of the invention in which the privacy-preserving computation is a Fully Homomorphic Encryption (FHE) scheme.

Fully Homomorphic Encryption (FHE)—A third exemplary embodiment of the techniques presented in this disclosure is described below with reference to FIG. 4. This third exemplary embodiment is referred to herein as the 'Fully Homomorphic Encryption' embodiment 150 or the 'FHE' embodiment 150. FIG. 4 is a signalling and flow diagram that shows the information exchange and processing steps for a server 4 and a first client node 6 that submits a first event for evaluation. FIG. 4 also shows the information exchange and processing steps for the server 4 and a second client node 6 that submits a second event for evaluation.

Fully Homomorphic Encryption (FHE) is an encryption scheme that allows computation of both E(a+b) and E(a*b) without interactions between the two parties, thus basically allowing the same application as multi-party computation (MPC) with no interactions.

Therefore, FHE allows the server 4 to perform the complete evaluation of the monitoring function under encryption, without interaction with the client node 6. All that is required is for the client node 6 to encrypt the event $e_i$ using the system's public key pk and send it to the server 4. However, it will be appreciated that this only allows the server 4 to compute encryptions of the outputs t and o (e.g. $E_{pk}(t)$ and $E_{pk}(o)$ respectively), which still need to be decrypted. The server 4 cannot have direct access to the private key sk needed for this decryption, since that would also allow the server 4 to decrypt the events. There are three ways in which this problem could be addressed.

Firstly, the client node 6 could have access to a secret key sk. After computation the server 4 sends $E_{pk}(t)$ to the client node 6, and the client node 6 decrypts to determine t. This solution means that every client node 6 (but not the server 4) needs access to the secret key sk, but client nodes 6 can decrypt events encrypted by other client nodes 6.

In a second approach, re-encryption can be used, for example as described in "Fully homomorphic encryption using ideal lattices" by Craig Gentry in: Proceedings of the 41$^{st}$ Annual ACM Symposium on Theory of Computing, STOC 2009, Bethesda, Md., USA, May 31-Jun. 2, 2009. In this case there will be a master public key pk and client node-specific public keys pk'. The client node has a secret key sk', and the server 4 has access to an encryption of sk under key pk', i.e. $E_{pk'}(sk)$. The events will be encrypted by the client node 6 using pk, and the server 4 performs all computations using that key to find $E_{pk}(t)$ and $E_{pk}(o)$. The server 4 then re-encrypts the output to $E_{pk'}(t)$ and $E_{pk'}(o)$, which can be decrypted by the client node 6 using sk'. This solution means that every client node 6 can have a different pk'/sk'.

In a third approach, as described in "Threshold Fully Homomorphic Encryption and Secure Computation" by Steven Myers, Mona Sergi, and Abhi Shelat in IACR Cryptology ePrint Archive 2011 (2011), p. 454, a variant of FHE with threshold decryption is proposed. As in THE, this requires the server 4 and client node 6 to work together in an interactive protocol to perform a decryption. However here only the outputs t and o needs to be decrypted interactively, as opposed to (non-fully) homomorphic threshold encryption where the whole computation is an interactive protocol.

In each of the above approaches, the general operations of the server 4 and client nodes 6 is as follows. Thus, in FIG. 4 the FHE encryption scheme has been set up, with a public key pk available to the server 4 and all client nodes 6 (as indicated by box 152), and the secret keys distributed according to one of the above approaches.

A client node 6 can start the FHE-based two-party protocol with the server 4. At the start, it is assumed that neither the server 4 nor client node 6 have a current state in relation to the evaluation function to be monitored.

Firstly, a first client node 6 has an event $e_1$ that has been measured, observed or obtained by the first client node 6 that is to be evaluated. The first client node 6 encrypts the event $e_1$ using pk and sends the encrypted event $E_{pk}(e_1)$ to the server 4 (signal 154).

The server 4 evaluates the monitoring function as a privacy-preserving computation to compute $E_{pk}(t)$ and $E_{pk}(o)$ based on the input $E_{pk}(e_1)$ (step 156). The encrypted outputs $E_{pk}(t)$ and $E_{pk}(o)$ are then sent to the first client node 6 (signal 158). The evaluation of the monitoring function also results in the server 4 having an encrypted monitoring state S (denoted E(S), as indicated by box 160).

Next, the first client node 6 decrypts $E_{pk}(t)$ to find t, and sends t back to the server 4. In some embodiments, this decryption simply comprises the first client node 6 decrypting the encrypted outputs using the secret key. However, in further embodiments, this decryption can also involve an exchange of messages or signals between the server 4 and the first client node 6 to verify that the decryption has been performed correctly and/or that the first client node 6 does not provide the server 4 with a false decryption of the output (i.e. to make sure that the first client node 6 does not 'lie' about the result of the decryption). The decryption is indicated by signals 162 in FIG. 4.

If the decryption of $E_{pk}(t)$ indicates that t=1 (i.e. the trigger condition is satisfied), then the first client node 6 and the server 4 can decrypt $E_{pk}(o)$ to find o. This can be performed in the same way as the decryption of t (and is also covered by the signalling 162 in FIG. 4).

The server 4 stores the encrypted state S (i.e. stores E(S))—step 164, so that it can use this monitoring state of the monitoring function in the next evaluation. The server 4 is not able to learn the contents of the monitoring state S, since it requires assistance from the first client node 6 to decrypt E(S).

When another client node 6 (or even the first client node 6) has another event to evaluate, the server 4 can continue the FHE protocol as follows. Thus, a second client node 6 has an event $e_2$ that has been measured, observed or obtained by the second client node 6. The second client node 6 encrypts the event $e_2$ using the public key pk and sends the encrypted second event $E_{pk}(e_2)$ to the server 4 (signal 166).

The server 4 evaluates the monitoring function as a privacy-preserving computation to compute $E_{pk}(t)$ and $E_{pk}(o)$ based on the input $E_{pk}(e_2)$ (step 168). The encrypted outputs $E_{pk}(t)$ and $E_{pk}(o)$ are then sent to the second client node 6 (signal 170). The evaluation of the monitoring function also results in the server 4 having an encrypted updated monitoring state S' (denoted E(S'), as indicated by box 172).

Next, the second client node 6 decrypts $E_{pk}(t)$ to find t, and sends t back to the server 4 (signal 174). This decryption can be the same as that performed by the first client node 6 in step 162 above.

If the decryption of $E_{pk}(t)$ indicates that t=1 (i.e. the trigger condition is satisfied), then the second client node 6 and the server 4 can decrypt $E_{pk}(o)$ to find o. This can be performed in the same way as the decryption of t.

The server 4 stores the encrypted updated monitoring state S' (i.e. stores E(S'))—step 176, so that it can use this monitoring state of the monitoring function in the next evaluation. Again, the server 4 is not able to learn the contents of the updated monitoring state S', since it requires assistance from the second client node 6 to decrypt E(S').

Garbled circuits—In some implementations of the techniques described herein, the two-party computations can be effected using so-called 'garbled circuits'. Garbled circuits are an intrinsically asymmetric technique in which one party acts as the 'garbler' and sets up an encrypted binary circuit to compute a function f, and sends this to the other party. This 'garbled circuit' can be used to obliviously compute f, without the other party seeing the state during computation. The garbler's private input is already embedded in the circuit. Garbling can be done using, e.g., GaX which is described in "Efficient Garbling from a Fixed-Key Blockcipher" by Mihir Bellare et al., IACR Cryptology ePrint Archive 2013 (2013), p. 426. The other party acts as 'evaluator' to the circuit. To do this the other party needs to obtain from the garbler special keys related to his private input wires. These keys can be obtained using 1-out-of-2 oblivious transfer, for example as described in "The Simplest Protocol for Oblivious Transfer" by Tung Chou and Claudio Orlandi in Progress in Cryptology—LATINCRYPT 2015-4th International Conference on Cryptology and Information Security in Latin America, Guadalajara, Mexico, Aug. 23-26, 2015, Proceedings. The output of the circuit is either public to the evaluator, or consists of output wire keys that can be decoded by the garbler.

To implement the above techniques for evaluating a monitoring function using garbled circuits, there are two requirements. Firstly the triggering of the trigger condition should be identifiable, and secondly the state of one computation needs to be transferred to the next one.

The solution to this is to have a series of garbled circuits, one for each event. Each of these circuits can have one easily recognisable output wire for output t, which will signal whether or not the trigger condition was satisfied. Triggering this condition can lead to the decryption of parts of the state as output o. The state between two computations is signified by a group of output wire keys that will be reused as input wire keys to the next computation. Between computations the garbler will keep all the output wire keys for both 0 and 1 wires as a state, without knowing which ones were evaluated. The evaluator will compute either the 0 or 1 wire keys during evaluation, without knowing what they signify, and keep them as a state. On the next computation the evaluator will use these wire keys as input wires, without needing to do an oblivious transfer (OT).

Where garbled circuits are used, either the server 4 or the current client node 6 can act as the garbler. In either case, the client node 6 has a state that must be passed on to the next client node 6. This can be done just as in the generic embodiment shown in FIG. 2.

Figure 5:
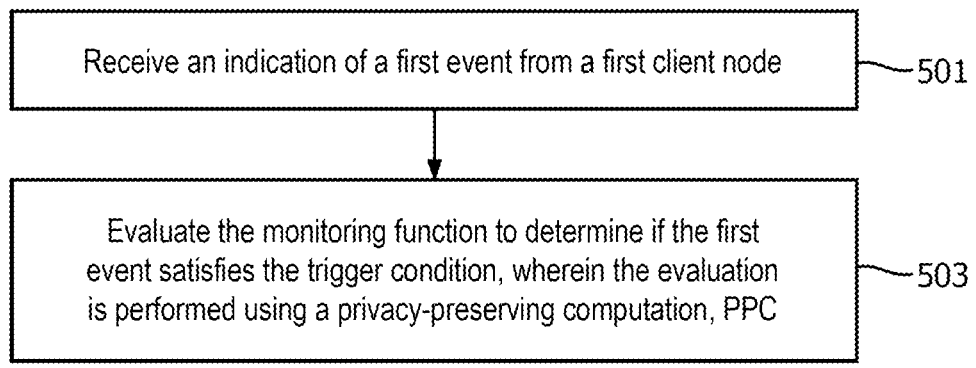
FIG. 5 is a flow chart illustrating a method of operating a server according to an embodiment.

The flow chart in FIG. 5 illustrates a general method of operating a server 4 according to embodiments of the invention. The method is for evaluating a monitoring function to determine if a trigger condition is satisfied. The method can be performed by the processing unit 12, for example by executing suitable computer program code stored in the memory unit 14. At the start of the method, the server 4 may store (or have stored) a current monitoring state Ss of the server 4 or an encrypted current monitoring state S of the monitoring function in a memory unit 14. As described above, the current monitoring state Ss of the server 4 relates to the current monitoring state S of the monitoring function that is based on an evaluation of one or more previous events.

In a first step, step 501, the server 4 receives an indication of a first event from a first client node 6. This indication can be received using interface circuitry 10. This indication can be an indication that an event is to be evaluated, rather than the event itself (since the client node 6 intends for the event to be kept secret from the server 4).

The receipt of the indication leads to the server 4 evaluating the monitoring function to determine if the first event satisfies the trigger condition (step 503). The evaluation is performed using or as a privacy-preserving computation, PPC, as described above. As part of this evaluation, in some embodiments the server 4 provides the current monitoring state Ss of the server 4 as a first private input to the PPC (e.g. as in the generic embodiment shown in FIG. 2) and in other embodiments provides the encrypted current monitoring state S of the monitoring function as a first input to the PPC (e.g. as in the THE and FHE embodiments shown in FIGS. 3 and 4 respectively). The first client node 6 provides the first event (e.g. as in the generic embodiment and THE embodiments shown in FIGS. 2 and 3 respectively) or an encryption thereof (e.g. as in the FHE embodiment shown in FIG. 4) as a private input to the PPC.

The evaluation of the monitoring function in step 503 provides an encrypted updated monitoring state S' of the monitoring function (e.g. as in the THE and FHE embodiments shown in FIGS. 3 and 4 respectively) or an updated monitoring state Ss' of the server (e.g. as in the generic embodiment shown in FIG. 2) as an output o of the monitoring function and an indication t of whether the first event satisfies the trigger condition.

As described above, the PPC is a computation in which the server 4 does not share the current monitoring state Ss of the server 4 (or the current monitoring state of the monitoring function S) with the first client node 6 and in which the first client node 6 does not share the first event with the server 4. In other words, the PPC is a computation in which the server 4 keeps the current monitoring state Ss of the server 4 (or the current monitoring state of the monitoring function S) secret from the first client node 6 and in which the first client node 6 keeps the first event secret from the server 4.

As described above, the PPC is a multi-party computation, MPC, with the server 4 and the first client node 6 as the parties to this MPC. In some embodiments, the MPC is threshold homomorphic encryption (THE). In alternative embodiments, the PPC is Fully Homomorphic Encryption (FHE) that does not require the involvement of the first client node 6 in the computation (other than submitting an encrypted event).

In further embodiments, the method can further comprise outputting the indication t of whether the first event satisfies the trigger condition. In some embodiments, if the first event satisfies the trigger condition, the method can further comprise providing a public output o of the monitoring function.

The following steps, actions and features relate to the generic embodiment shown in FIG. 2.

In the generic embodiment, the PPC is a multi-party computation between the server 4 and the first client node 6. The first client node 6 provides a current monitoring state Sc of the first client node 6 as a second private input to the PPC (i.e. in addition to the first event), with the current monitoring state Ss of the server 4 and the current monitoring state Sc of the first client node 6 together forming the encrypted current monitoring state S of the monitoring function.

The method can also comprise the server 4 storing an encrypted current monitoring state Sc of a client node 6 from an earlier evaluation of the monitoring function, and before performing step 503 (corresponding to step 56 in FIG. 2), sending the encrypted current monitoring state Sc of a client node to the first client node 6 after receiving the indication of a first event. In this way the first client node 6 can resume a PPC started with another client node 6.

In the generic embodiment the result of step 503 provides an updated monitoring state Sc' of the first client node 6 and an updated monitoring state Ss' of the server 4, with these updated states together forming an encrypted updated monitoring state S' of the monitoring function. After step 503 the method can further comprise the server 4 receiving an encrypted updated monitoring state $E_{sk}(Sc')$ of the first client node 6 from the first client node 6 (e.g. corresponding to signal 66 in FIG. 2). The method can then comprise the server 4 storing $E_{sk}(Sc')$ in the memory unit 14.

After completion of the evaluation of the first event, the method may further comprise the server 4 receiving an indication of a second event from a second client node 6 (e.g. as in signal 70 of FIG. 2). After receiving this indication, the method further comprises sending the encrypted updated monitoring state $E_{sk}(Sc')$ of the first client node 6 to the second client node 6 (e.g. corresponding to signal 72 in FIG. 2). This enables the second client node 6 to resume the PPC with the server 4.

The method then comprises evaluating the monitoring function as a PPC with the second client node 6 to determine if the second event satisfies the trigger condition (block 76 in FIG. 2). In this evaluation the server 4 provides the updated monitoring state Ss' of the server 4 as a private input to the PPC and the second client node 6 provides the second event or an encryption thereof and the updated monitoring state Sc' of the first client node 6 as private inputs to the PPC. The evaluation provides a further updated monitoring state of the server (denoted Ss") as a private output of the monitoring function and an indication t of whether the second event satisfies the trigger condition. The further updated monitoring state Ss" of the server 4 forms an encrypted further updated monitoring state of the monitoring function (denoted S") together with a further updated monitoring state of the second client node 6 (denoted Sc").

The following steps, actions and features relate to the THE embodiment shown in FIG. 3.

In these embodiments, the PPC is THE and the method further comprises the server 4 storing a public key of a THE scheme and a first key share for a private key of the THE scheme. As described above, the first key share can be combined with a second key share for the private key stored by the first client node 6 to determine the private key. In some embodiments, the server 4 may store respective key share for each of the client nodes 6 in the system 2.

In the THE embodiment, the evaluation of the monitoring function in step 503 provides the encrypted updated monitoring state S' of the monitoring function. The method further comprises storing the encrypted updated monitoring state S' of the monitoring function, for example in the memory unit 14.

After completion of the evaluation of the first event, the method can further comprise receiving an indication of a second event from a second client node 6. In that case, the server 4 sends the stored encrypted updated monitoring state S' of the monitoring function to the second client node 6 (e.g. as shown by signal 124 in FIG. 3). The method then comprises evaluating the monitoring function as or using PPC to determine if the second event satisfies the trigger condition (e.g. as shown as step 126 in FIG. 3). For this evaluation the server 4 provides the encrypted updated monitoring state S' of the monitoring function as a first private input to the PPC and the second client node 6 provides the second event or an encryption thereof and the encrypted updated monitoring state S' of the monitoring function as second private inputs to the PPC. The evaluation provides an encrypted further updated monitoring state S" of the monitoring function as an output and an indication t of whether the second event satisfies the trigger condition.

The following steps, actions and features relate to the FHE embodiment shown in FIG. 4.

In these embodiments, the PPC is FHE and the method further comprises the server 4 storing a public key of a FHE scheme, for example in the memory unit 14. In addition, the indication of the first event received from the first client node 6 in step 501 is encrypted using the public key.

The evaluation of the monitoring function in step 503 provides an encrypted indication of whether the first event satisfies the trigger condition, and the method further comprises sending the encrypted indication of whether the first event satisfies the trigger condition to the first client node 6 for decryption.

After the evaluation of the first event has been completed, the method in the server 4 may further comprise the steps of receiving an encrypted second event (that is encrypted using the public key of the FHE scheme) from a second client node 6, and evaluating the monitoring function to determine if the second event satisfies the trigger condition. This evaluation provides an encrypted further updated monitoring state S" of the monitoring function as an output and an encrypted indication of whether the second event satisfies the trigger condition. The method then comprises sending this encrypted indication to the second client node 6 for decryption.

Figure 6:
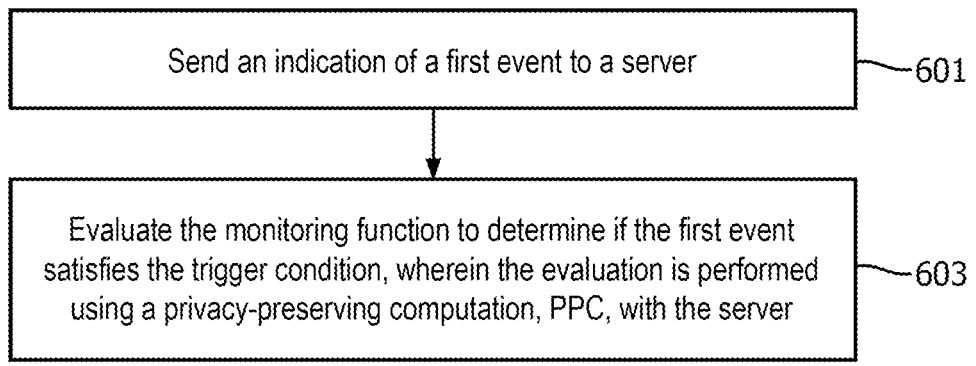
FIG. 6 is a flow chart illustrating a method of operating a client node according to an embodiment.

The flow chart in FIG. 6 illustrates a general method of operating a client node 6 according to embodiments of the invention. The method is for evaluating a monitoring function to determine if a trigger condition is satisfied. It will be appreciated that the method in FIG. 6 is not applicable to the FHE embodiment, since in that embodiment the server 4 performs the evaluation of the monitoring function without interaction with the client node 6. The method in FIG. 6 can be performed by the processing unit 18, for example by executing suitable computer program code stored in the memory unit 20.

In a first step, step 601, the client node 6 sends an indication of a first event to a server 4. This indication can be sent using interface circuitry 16. This indication can be an indication that an event is to be evaluated, rather than the event itself (since the client node 6 intends for the event to be kept secret from the server 4).

The client node 6 then evaluates the monitoring function to determine if the first event satisfies the trigger condition (step 603). The evaluation is performed using a privacy-preserving computation, PPC, with the server 4. As part of the PPC, the server 4 provides a current monitoring state Ss of the server 4 (e.g. as in the generic embodiment shown in FIG. 2) or an encrypted current monitoring state S of the monitoring function as a first private input to the PPC (e.g. as in the THE embodiment shown in FIG. 3). The first client node 6 provides a current monitoring state Sc of the first client node (e.g. as in the generic embodiment shown in FIG. 2) or an encryption of the current monitoring state S of the monitoring function (e.g. as in the THE embodiment shown in FIG. 3) and the first event (e.g. as in the generic embodiment and THE embodiments shown in FIGS. 2 and 3 respectively) or an encryption thereof as second private inputs to the PPC.

The evaluation of the monitoring function in step 603 provides an encrypted updated monitoring state S' of the monitoring function (e.g. as in the THE embodiment shown in FIG. 3) or an updated monitoring state Sc' of the first client node (e.g. as in the generic embodiment shown in FIG. 2) as an output of the monitoring function and an indication t of whether the first event satisfies the trigger condition.

In some embodiments, the method further comprises receiving the indication t of whether the first event satisfies the trigger condition from the server 4. In further embodiments, the method further comprises receiving a public output o of the monitoring function if the first event satisfies the trigger condition.

In the generic embodiment, the PPC is a multi-party computation (MPC) with the server 4. The first client node 6 provides a current monitoring state Sc of the first client node 6 as a second private input to the PPC. The current monitoring state Ss of the server 4 and the current monitoring state Sc of the first client node 6 together form the encrypted current monitoring state S of the monitoring function.

A secret key sk may be stored in the memory unit 20 and the method may further comprise the steps of receiving an encrypted current monitoring state Sc of a client node from the server 4 (for example using interface circuitry 16) after sending the indication of the first event in step 601 (this step corresponds to signal 72 in FIG. 2), and decrypting the encrypted current monitoring state Sc of a client node 6 to determine the current monitoring state Sc (this corresponds to step 74 in FIG. 2). The method can then comprise using the current monitoring state Sc as the second private input to the PPC.

The evaluation of the monitoring function can provide an updated monitoring state Sc' of the first client node 6 and an updated monitoring state Ss' of the server 4, where the updated monitoring state Sc' of the first client node 6 and the updated monitoring state Ss' of the server 4 together form an encrypted updated monitoring state S' of the monitoring function.

The method can then further comprise encrypting the updated monitoring state Sc' of the first client node 6 using the secret key 52 and sending the encrypted updated monitoring state $E_{sk}(Sc')$ to the server 4 (as indicated by signal 66 in FIG. 2).

In the Threshold Homomorphic Encryption embodiment, the PPC is Threshold Homomorphic Encryption, THE, and the client node 6 stores a public key of a THE scheme and a second key share for a private key of the THE scheme. The second key share can be combined with a first key share for the private key stored by the server 4 to determine the private key.

In the THE embodiment, the evaluation of the monitoring function in step 603 provides the encrypted updated monitoring state S' of the monitoring function, and the method further comprises the first client node 6 discarding the encrypted updated monitoring state S'.

In some embodiments, the method further comprises receiving an encrypted current monitoring state S of the monitoring function from the server 4 after sending the indication of the first event in step 601 (e.g. corresponding to signal 124 in FIG. 3), and using the encrypted current monitoring state S as the second private input to the PPC.

It will be appreciated that the techniques according to the invention could be used for evaluating monitoring functions and events in many different areas and technical fields. Some examples are set out below.

Air quality—It may be desirable to cross-correlate information on air pollution with test results for breathing problems, to monitor if there are significant concerns. While air pollution levels could be public information, the test results on breathing problems are sensitive and distributed over various doctors, GPs and hospitals. Every time a test is taken, the test results and area code could be encrypted by the relevant GP and sent to the server. The trigger condition will be to raise an alarm if in any area the test results are significantly worse than normal.

Security Analytics—Servers keep activity logs. These logs can be used to detect attacks. An example is repeated log-in attempts from the same remote system. However, it is not always necessary to keep logs of identities for all honest users. The techniques described herein can be used to combine logging information from many different systems and perform anomaly detection. The trigger condition will be to raise an alarm and release and identity if such an anomaly has been detected.

Financial market manipulation—A framework for monitoring financial markets for market manipulation could enable the use of sensitive data, i.e. facts and insights from banks and/or traders that they would not otherwise make public. The trigger condition would be to raise an alarm and release proof when the monitoring framework identifies possible market manipulation.

Canvas cutters/Object surveillance—This involves detecting bad or suspicious behaviour involving vehicles. The first relates to criminals frequently looting trucks parked at rest stops by cutting the canvas that protects the goods. The second is about criminals casing the location of upcoming criminal activities. One way to detect these criminals is to use a camera to look for vehicles that enter several different rest stops within a couple of hours, together with some other observable behavior. These vehicle are suspicious. Other passing vehicles should remain anonymous. Using the techniques described herein, every registered vehicle could be an event. The trigger condition would be to raise an alarm and release their license plate information when a vehicle has been flagged as suspicious.

Average speed checking—Some countries have deployed average speed checking systems that measure a vehicle's speed along a stretch of road. This requires some form of storage to determine the time it took to traverse a stretch of road. Using the techniques described herein, it could be determined that a vehicle has passed two measuring stations too fast and release its licence plate, while keeping all other cars anonymous.

There is therefore provided improved techniques for evaluating a monitoring function to determine if a trigger condition is satisfied when one or more of the parties involved is unwilling or unable to share relevant information, such as event information.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A server for use in evaluating a monitoring function to determine if a trigger condition is satisfied, the server comprising:
    a memory unit for storing a current monitoring state Ss of the server or an encrypted current monitoring state S of the monitoring function, the current monitoring state Ss of the server relating to the current monitoring state S of the monitoring function that is based on an evaluation of one or more previous events; and
    a processing unit configured to:
        receive an indication of a first event from a first client node;
        evaluate the monitoring function to determine if the first event satisfies the trigger condition, wherein the evaluation is performed using a privacy-preserving computation, PPC,
            wherein the server is configured to provide the current monitoring state Ss of the server as a first private input to the PPC or the encrypted current monitoring state S of the monitoring function as a first input to the PPC, and the PPC comprises the first event or an encryption thereof as a private input to the PPC of the first client node, wherein the current monitoring state is kept secret from the first client node and the first event is kept secret from the server,
            wherein the evaluation of the monitoring function provides an encrypted updated monitoring state S' of the monitoring function or an updated monitoring state Ss' of the server as an output of the monitoring function and an indication of whether the first event satisfies the trigger condition, and
            wherein the server receives, from the first client node after the PPC, an encrypted updated monitoring state Sc' of the first client node, wherein the updated monitoring state is encrypted with a secret key of the first client node.

2. A server as claimed in claim 1, wherein the server is additionally configured to receive an indication of a second event from a second client node and to evaluate the monitoring function as a PPC with the second client node to determine if the second event satisfies the trigger condition.

3. A server as claimed in claim 1, wherein the PPC is a multi-party computation, MPC, with the first client node, wherein the PPC comprises the current monitoring state Sc of the first client node as a second private input of the first client node to the PPC, wherein the current monitoring state Ss of the server and the current monitoring state Sc of the first client node together form the encrypted current monitoring state S of the monitoring function.

4. A server as claimed in claim 3, wherein the memory unit is for storing an encrypted current monitoring state Sc of a client node, and wherein the processing unit is further configured to send the encrypted current monitoring state Sc of a client node to the first client node after receiving the indication of a first event.

5. A server as claimed in claim 1, wherein the PPC is Threshold Homomorphic Encryption, THE, and wherein the memory unit is further for storing a public key of a THE scheme and a first key share for a private key of the THE scheme, wherein the first key share can be combined with a second key share for the private key stored by the first client node to determine the private key.

6. A server as claimed in claim 1, wherein the PPC is Fully Homomorphic Encryption, FHE, wherein the memory unit is further for storing a public key of a fully homomorphic encryption scheme, and wherein the indication of the first event from the first client node is an encrypted first event that is encrypted using the public key.

7. A system for use in evaluating a monitoring function to determine if a trigger condition is satisfied, the system comprising:
    a server as claimed in claim 1; and
    at least one first client node.

8. A method of operating a server to evaluate a monitoring function to determine if a trigger condition is satisfied, the server storing a current monitoring state Ss of the server or an encrypted current monitoring state S of the monitoring function, the current monitoring state Ss of the server relating to the current monitoring state S of the monitoring function that is based on an evaluation of one or more previous events;
    wherein the method comprises:
        receiving an indication of a first event from a first client node;
        evaluating the monitoring function to determine if the first event satisfies the trigger condition, wherein the evaluation is performed using a privacy-preserving computation, PPC;
            wherein the server provides the current monitoring state Ss of the server as a first private input to the PPC or the encrypted current monitoring state S of the monitoring function as a first input to the PPC, and the PPC comprises the first event or an encryption thereof as a private input to the PPC of the first client node, wherein the current monitoring state is kept secret from the first client node and the first event is kept secret from the server,
            wherein the evaluation of the monitoring function provides an encrypted updated monitoring state S' of the monitoring function or an updated monitoring state Ss' of the server as an output of the monitoring function and an indication of whether the first event satisfies the trigger condition; and
        receiving from the first client node after the PPC, an encrypted updated monitoring state Sc' of the first client node, wherein the updated monitoring state is encrypted with a secret key of the first client node.

9. A computer program product comprising a computer readable medium having computer readable code embodied therein, the computer readable code being configured such that, on execution by a suitable computer or processor, the computer or processor is caused to perform the method of claim 8.

10. A first client node for use in evaluating a monitoring function to determine if a trigger condition is satisfied, the first client node comprising:
- a processing unit configured to:
  - send an indication of a first event to a server,
  - evaluate the monitoring function to determine if the first event satisfies the trigger condition, wherein the evaluation is performed using a privacy-preserving computation, PPC, with the server,
    - wherein the PPC comprises a current monitoring state Ss of the server or an encrypted current monitoring state S of the monitoring function as a first private input to the PPC of the server and the first client node is configured to provide (i) a current monitoring state Sc of the first client node or an encryption of the current monitoring state S of the monitoring function; and (ii) the first event or an encryption thereof, as second private inputs to the PPC, wherein the current monitoring state is kept secret from the first client node and the first event is kept secret from the server,
    - wherein the evaluation of the monitoring function provides an encrypted updated monitoring state S' of the monitoring function or an updated monitoring state Sc' of the first client node as an output of the monitoring function and an indication of whether the first event satisfies the trigger condition; and
  - send to the server after the PPC, an encrypted updated monitoring state Sc' of the first client node, wherein the updated monitoring state is encrypted with a secret key of the first client node.

11. A first client node as claimed in claim 10, wherein the PPC is a multi-party computation, MPC, with the server, wherein the first client node is configured to provides the current monitoring state Sc of the first client node as a second private input to the PPC, wherein the current monitoring state Ss of the server and the current monitoring state Sc of the first client node together form the encrypted current monitoring state S of the monitoring function.

12. A first client node as claimed in claim 11, wherein the PPC is Threshold Homomorphic Encryption, THE, and wherein the memory unit is further for storing a public key of a THE scheme and a second key share for a private key of the THE scheme, wherein the second key share can be combined with a first key share for the private key stored by the server to determine the private key.

13. A method of operating a first client node to evaluate a monitoring function to determine if a trigger condition is satisfied, the method comprising:
- sending an indication of a first event to a server,
- evaluating the monitoring function to determine if the first event satisfies the trigger condition, wherein the evaluation is performed using a privacy-preserving computation, PPC, with the server,
  - wherein the PPC comprises a current monitoring state Ss of the server or an encrypted current monitoring state S of the monitoring function as a first private input to the PPC of the server and the first client node provides (i) a current monitoring state Sc of the first client node or an encryption of the current monitoring state S of the monitoring function; and (ii) the first event or an encryption thereof, as second private inputs to the PPC, wherein the current monitoring state is kept secret from the client and the first event is kept secret from the server,
  - wherein the evaluation of the monitoring function provides an encrypted updated monitoring state S' of the monitoring function or an updated monitoring state Sc' of the first client node as an output of the monitoring function and an indication of whether the first event satisfies the trigger condition; and
- sending to the server after the PPC, an encrypted updated monitoring state Sc' of the first client node, wherein the updated monitoring state is encrypted with a secret key of the first client node.

14. A computer program product comprising a computer readable medium having computer readable code embodied therein, the computer readable code being configured such that, on execution by a suitable computer or processor, the computer or processor is caused to perform the method of claim 13.

* * * * *